(12) United States Patent
Marrone et al.

(10) Patent No.: US 12,012,372 B2
(45) Date of Patent: Jun. 18, 2024

(54) PROCESS AND PLANT FOR THE SYNTHESIS OF UREA

(71) Applicant: Casale SA, Lugano (CH)

(72) Inventors: Leonardo Marrone, Mercallo (IT); Paolo Bertini, Lugano (CH); Matteo Fumagalli, San Fermo della Battaglia (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 17/802,101

(22) PCT Filed: Feb. 9, 2021

(86) PCT No.: PCT/EP2021/053036
§ 371 (c)(1),
(2) Date: Aug. 24, 2022

(87) PCT Pub. No.: WO2021/170391
PCT Pub. Date: Sep. 2, 2021

(65) Prior Publication Data
US 2023/0118984 A1  Apr. 20, 2023

(30) Foreign Application Priority Data
Feb. 25, 2020 (EP) .................... 20159396

(51) Int. Cl.
*C07C 273/04* (2006.01)
*B01J 19/24* (2006.01)

(52) U.S. Cl.
CPC ......... *C07C 273/04* (2013.01); *B01J 19/2465* (2013.01); *B01J 2219/00162* (2013.01)

(58) Field of Classification Search
None
See application file for complete search history.

(56) References Cited

U.S. PATENT DOCUMENTS

| | | | | |
|---|---|---|---|---|
| 2003/0088126 A1* | 5/2003 | Mennen | ...................... | B01J 3/04 422/609 |
| 2005/0038293 A1* | 2/2005 | Jonckers | ............... | C07C 273/04 564/67 |

FOREIGN PATENT DOCUMENTS

| | | | | |
|---|---|---|---|---|
| EP | 0155735 | * | 9/1985 | .......... C07C 126/02 |
| EP | 1036787 A1 | | 9/2000 | |

(Continued)

OTHER PUBLICATIONS

International Search Report dated Feb. 26, 2021 issued in connection with PCT/EP2021/053036.

(Continued)

*Primary Examiner* — Amy C Bonaparte
(74) *Attorney, Agent, or Firm* — Akerman LLP

(57) ABSTRACT

A process for synthesis of urea from ammonia and carbon dioxide wherein: the urea synthesis is performed with a stripping process in a synthesis loop including at least a reactor (1), a stripper (2) and a condenser (3); the reactor effluent is treated in the stripper to remove unreacted ammonia and carbon dioxide; the urea solution (14) from the stripper is sent to a low-pressure recovery section (4); the stripper vapours are split into a first portion (151) directed to the reactor and a second portion (152) sent to the condenser; the condenser (3) is a shell-and-tube kettle condenser where condensation of stripper vapours is performed in the tube side (30); a carbamate-containing effluent (20) from the condenser is returned to the reactor.

20 Claims, 1 Drawing Sheet

(56) References Cited

FOREIGN PATENT DOCUMENTS

| EP | 2297094 A1 | 3/2011 |
| WO | 9931053 A1 | 6/1999 |
| WO | 2019/083367 A1 | 5/2019 |

OTHER PUBLICATIONS

Written Opinion of the International Searching Authority dated Feb. 26, 2021 issued in connection with PCT/EP2021/053036.
International Preliminary Report on Patentability dated Jun. 10, 2022 issued in connection with PCT/EP2021/053036.
Messen, "Urea," Ullmann's Encyclopedia of Industrial Chemistry, Wiley-VCH Verlag, 2010.
Xu et al., "Application of Pool Condenser in Urea Device Using Improved CO2 Stripping Process," Fertilizer Industry 2003.

* cited by examiner

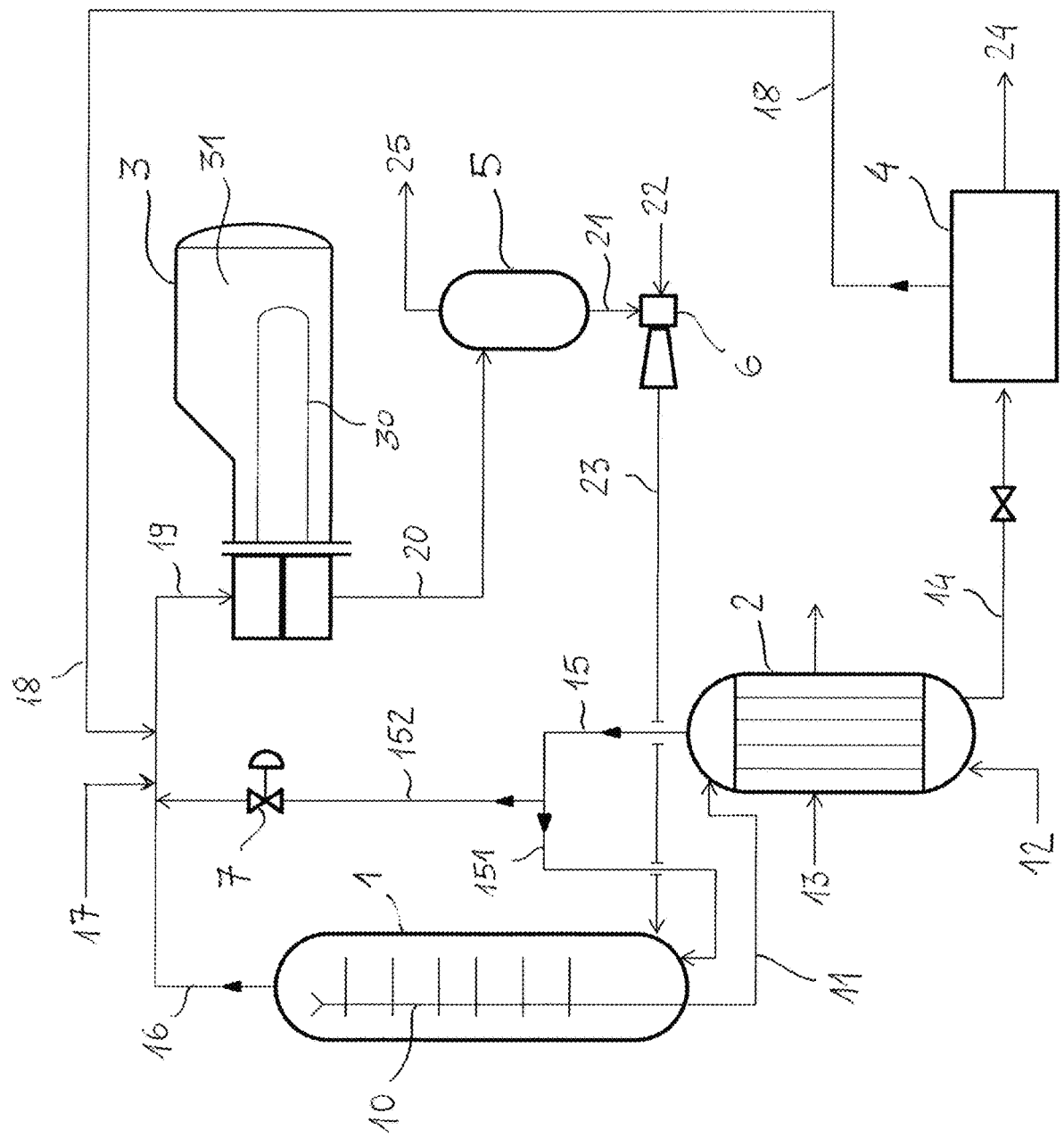

PROCESS AND PLANT FOR THE SYNTHESIS OF UREA

CROSS-REFERENCE TO RELATED APPLICATIONS

This application is a national phase of PCT/EP2021/053036, filed Feb. 9, 2021, and claims priority to EP 20159396.9, filed Feb. 25, 2020, the entire contents of both of which are hereby incorporated by reference.

FIELD OF APPLICATION

The invention relates to a process and plant for the synthesis of urea. Particularly the invention relates to improvements of the CO2-stripping process for the synthesis of urea.

PRIOR ART

An overview of the industrial processes for the synthesis of urea can be found in Meessen, "Urea", Ullmann's Encyclopedia of Industrial Chemistry, Wiley-VCH Verlag, 2010.

The CO2-stripping process is named after the use of gaseous CO2 as a stripping aid in the processing of the urea-containing effluent solution withdrawn from the reactor. This stripping step is normally performed in a steam-heated shell-and-tube stripper wherein the reactor effluent flows through the tube side in a falling-film regime and gaseous CO2 is fed in counter-current from the bottom of tubes. The heat furnished by the hot steam causes the dissociation of the unconverted ammonium carbamate contained in the solution and the gaseous CO2 reduces the partial pressure of ammonia favouring the decomposition of carbamate.

The stripping step therefor results in a urea solution collected at the bottom of the stripper, with a reduced content of unconverted ammonium carbamate, and a stream of stripper overhead gas predominantly composed of ammonia and carbon dioxide.

The urea solution is further processed in a recovery section to remove unconverted carbamate. The overhead gaseous stream is condensed in a high-pressure condenser normally with the help of a recycle carbamate solution and the so obtained condensate is sent back to the reactor. The cooling medium of the condenser is generally water evaporated to produce steam.

Accordingly a CO2 stripping plant normally comprises a high-pressure synthesis section including a reactor, a stripper, a condenser and a scrubber. Said items form a so-called high-pressure loop wherein the effluent of the reactor goes to the stripper, the overhead gas emerging from the stripper goes to the condenser, and the condensate withdrawn from the condenser is recycled back to the reactor.

A problem encountered in the CO2-stripping plants is to ensure a proper circulation between the items in this high-pressure synthesis loop. To this purpose, it may be necessary to install the items at different elevation, e.g. putting the scrubber above the condenser to ensure the flow of condensate from the scrubber to the condenser and putting the condenser above the reactor to ensure the flow of condensate from the condenser to the reactor. However this installation is expensive.

EP 2 297 094 discloses an evolution of the CO2 stripping process wherein the condenser is a horizontal kettle apparatus providing an additional synthesis space. The condenser is a shell-and-tube apparatus wherein condensation of the stripper gas is performed in the shell side and the cooling water is fed to the tube side.

This design may reduce the elevation of the equipment thanks to the horizontal layout of the condenser and the split of fresh CO2 between the reactor and the stripper. However this solution has drawbacks.

A first drawback is performing the condensation in the shell side which means that the entire pressure vessel of the condenser must resist the synthesis pressure (well above 100 bar) and the aggressive environment of the urea process fluids. Therefore the condenser of this design is quite expensive.

A second drawback is that deviating part of the fresh CO2 directly to the reactor penalizes the stripper ammonia efficiency.

WO 2019/083367 discloses a high pressure carbamate condenser for urea stripping plants.

SUMMARY OF THE INVENTION

The invention aims to improve the CO2-stripping urea process and related plants. Particularly the invention aims to reduce the cost of the equipment and to provide a low-elevation synthesis loop whose installation is simpler and less expensive compared to the current solutions. Accordingly another aim of the invention is to reduce the capital cost of the synthesis section of a CO2 stripping plant.

These aims are achieved with a process and plant according to the claims.

In the invention, the gaseous CO2 fed to the stripper represents the full amount of fresh CO2 input to the synthesis loop, i.e. there is no direct feed of CO2 to the reactor. A related advantage is optimum efficiency of the stripper.

The stripper overhead gas (also termed stripper vapours), i.e. the ammonia and carbon dioxide containing gas which emerges from the stripper, is split into a first portion sent to the reactor and a second portion sent to the condenser. This split of the stripper vapours can be performed in accordance with EP 1 036 787. A related advantage is that the accumulation of inert gases in the reactor are kept to a minimum.

The condenser is a shell-and-tube kettle condenser with a tube side and a shell side and said second portion of the stripper overhead gas is sent to the tube side for condensation. A related advantage is that the high-pressure and aggressive process fluids are confined in the tube side of the condenser. The shell side and particularly the large pressure vessel must not be designed to resist the high pressure and corrosive attack of the carbamate-containing urea solution. This reduces the capital cost of the condenser.

The carbamate-containing condensate stream withdrawn from the condenser is then recycled to the reactor.

A synthesis section according to the invention requires a reduced elevation for installation. The elevation can be further reduced in the preferred embodiments, e.g. with the provision of an ejector to feed the condensate stream to the reactor, and/or by adopting a vertical reactor with a modified design having a reduced height and increased size (for example diameter). Accordingly, the capital cost for the manufacturing and installation of the equipment of the synthesis section is competitive.

PREFERRED EMBODIMENTS OF THE INVENTION

The carbamate-containing condensate stream, which is withdrawn from the tube side of the condenser, may be recycled to the reactor as such or via a carbamate separator. Said carbamate separator may be provided to separate the effluent of the condenser, which is typically a biphasic mixture, into a carbamate-containing liquid and a vapour phase. The liquid is then sent to the reactor. The vapour phase may be composed predominantly of non-condensable gases and can be vented.

The carbamate containing liquid, preferably after the phase separation in the above mentioned carbamate separator, may be fed to the reactor via an ejector. More preferably the motive stream of the ejector is a stream of fresh ammonia. In an alternative embodiment the carbamate containing liquid may flow to the reactor by gravity. The embodiment with an ejector is preferred because it does not require to install the condenser above the reactor, hence the elevation of the equipment is reduced.

The fresh ammonia fed to the ejector may represent the majority of fresh ammonia input to the synthesis loop, preferably at least 80% of the fresh ammonia input. A remaining portion of fresh ammonia may enter the loop by mixing with the portion of the stripper overhead gas sent to the condenser.

According to various embodiments, the stripper overhead gas directed to the condenser may be mixed with one or more of: a stream of inert gas vented from the reactor; a stream of fresh ammonia; a carbamate-containing recycle solution coming from a recovery section. The mixing may be performed prior to introduction in the tube side of the condenser.

In an embodiment, the urea synthesis section (high-pressure loop) does not include a high pressure scrubber. Accordingly, a stream of inert gas vented from the reactor is mixed with the second portion of stripper vapours prior to introduction of said stripper vapours in the tube side of the condenser.

In a preferred embodiment, the portion of stripper overhead gas directed to the condenser is mixed with fresh ammonia, vent gas from the reactor and a carbamate recycle solution coming from a recovery section. The fresh ammonia so introduced in the condenser may be a minor part of the ammonia input to the synthesis loop, for example 20% or around 20%. The remaining portion may be introduced directly into the reactor, for example via the ejector, when provided.

The overhead gas of the reactor must be removed to avoid accumulation of inert gas in the reactor itself. The overhead gas that can be vented from top of the reactor however contains some ammonia and carbon dioxide. Mixing this reactor vent gas with the stripper gas directed to the condenser has the advantage that the reactants (ammonia and carbon dioxide) contained in the vent gas can be recovered via condensation.

Still another advantage of this embodiment is a possible improving of the overall efficiency of the process by transferring waste heat to the fresh ammonia fed to the synthesis loop, to preheat said fresh ammonia. All the heat provided to this stream is finally recovered in the condenser as low pressure steam usable in the recovery section. This gives the opportunity to decrease the stripper MP steam consumption up to approximately half the heat transferred to the ammonia in the preheater.

In a different embodiment, the reactor vent gas may be contacted with a carbamate recycle solution in a high-pressure scrubber, thus obtaining a solution which is sent to the tube side of the condenser.

Preferably the shell side of the condenser is traversed by a cooling fluid, which is preferably boiling water, at a pressure not greater than 6 bar, preferably 2 to 6 bar. The tubes of the condenser are preferably a bundle of U-tubes.

The condensation performed in the tube side (i.e. process side) of the condenser is preferably a total condensation. This term denotes that the gaseous phase is almost completely condensed into a liquid state apart from the unavoidable non-condensable fraction.

In a preferred embodiment the urea reactor is a vertical reactor having a height of less than 20 meters, preferably in the range 12 to 18 meters and more preferably 12 to 16 meters. This height is considerably less than the usual height of urea reactors, which is 20 to 35 meters. According to an aspect of the invention, this reduced height is compensated by an increased ratio of height over diameter (h/D).

The resulting structure, which supports the item of the high-pressure synthesis section, may have a maximum elevation not greater than 40 meters, for example 30 to 38 meters, compared to the usual 45 to 60 meters of the prior art. This is a considerable advantage in terms of installation cost.

A preferred embodiment includes: the condensate stream withdrawn from the condenser is fed to the urea synthesis reactor via an ejector; overhead gas from the reactor are removed to avoid accumulation of inert gas in the reactor itself; the reactor vent gas is mixed with the stripper gas directed to the condenser, in order to recover the ammonia and carbon dioxide contained in the vent gas; the stripper is a shell-and-tube vertical apparatus operating at the same pressure as the reactor; the condenser is a high-pressure equipment operating at the same pressure as the reactor and stripper; the reactor, the stripper and the condenser are interconnected to form a high-pressure synthesis loop.

The detailed description which follows relates to preferred embodiments, which are described by way of a non-limiting example.

BRIEF DESCRIPTION OF THE FIGURES

The FIGURE is a scheme of a urea synthesis process and plant according to an embodiment of the invention.

DETAILED DESCRIPTION

The FIGURE illustrates the following main items:
Urea reactor 1
High-pressure stripper 2
High-pressure condenser 3
Low-pressure recovery section 4
Carbamate separator 5
Ejector 6
Control valve 7.

Urea is formed in the reactor 1 under a high pressure, for example 140 bar. The urea reactor 1 is a vertical apparatus internally divided by plates. The urea-containing solution is collected with a downcomer 10 and goes to the stripper 2 via line 11.

The stripper 2 is a shell-and-tube vertical apparatus operating substantially at the same pressure as the reactor 1. The reactor effluent 11 is fed to the tube side of the stripper 2. Gaseous CO2 is fed to the bottom of the tube side via a line 12. The effluent solution thus descends the tubes in a falling-film regime in counter-current with the gaseous CO2. The shell side around the tubes is heated by steam entering at line 13.

In the stripper 2, some of the unreacted carbamate contained in the reactor effluent is decomposed into gaseous ammonia and carbon dioxide.

The solution effluent from the stripper 2 is sent to the recovery section 4 via line 14.

The stripper overhead gas, which is predominantly composed of ammonia and carbon dioxide, is withdrawn from the top of the stripper 2 with line 15.

This line 15 is split into a first line 151 going to the reactor 1 and a second line 152 going to the condenser 3. The flow rate of line 152 is controlled by the valve 7.

Accordingly, a first portion of the stripper overhead gas is returned to the reactor 1 and a second remaining portion is sent to the condenser 3 for condensation. Preferably the valve 7 is regulated so that the stream of line 151 directed to the reactor 1 is 20% to 40% of the total stream withdrawn from the stripper in line 15.

The condenser 3 is a horizontal kettle apparatus with a bundle 30 of U-tubes. The condenser 3 is also a high-pressure equipment operating at a pressure substantially equal to the pressure of the reactor 1 and stripper 2.

Said second portion (line 152) of stripper overhead gas is sent to the tube side of the condenser 3, as illustrated.

More particularly, the second portion of stripper overhead gas of line 152 is mixed with reactor vented gas 16, a stream of fresh ammonia 17 and a stream of recycled solution 18 from the recovery section 4.

Mixing of the stripper vapours 152 with any of said streams 16 (reactor vent gas), 17 (fresh ammonia) and 18 (carbamate recycle), or a combination thereof, is an optional; the FIGURE shows a preferred embodiment where the stripper vapours 152 mixes with all said streams 16, 17 and 18.

The so obtained mixed stream 19, which includes the portion of stripper vapours of line 152, is condensed in the tube side 30 of the condenser 3. The shell side 31 is traversed by a cooling fluid, e.g. boiling water (not shown).

The condenser effluent is sent to the carbamate separator 5 via line 20. The condenser effluent in line 20 is generally a biphasic mixture. This mixture is separated into a liquid fraction and a gaseous fraction in the carbamate separator 5. The liquid fraction leaves the separator 5 with line 21 and is returned to the reactor 1 by means of the ejector 6 and its output line 23. A stream 22 of fresh ammonia drives the ejector 6. The gaseous fraction separated in the separator 5 is made chiefly of non-condensable gas and can be vented via line 25.

The recovery section 4 operates at a low pressure, for example 2 to 6 bar. The recovery section 4 is known and does not need be described in detail. Basically this section includes at least a low-pressure carbamate decomposer and a low-pressure condenser; gaseous ammonia and carbon dioxide are removed from the urea solution in the decomposer, and said gas are condensed into a carbamate-containing recycle solution in the low-pressure condenser.

Accordingly the recovery section 4 produces the carbamate-containing solution 18 and a urea solution 24 which consists essentially of urea and water. As stated above, the carbamate solution 18 is preferably returned to the condenser 3 together with the portion 152 of stripper vapours. The carbamate solution 18 may help condensation of said stripper vapours in the condenser.

It can be noted that the reactor 1, the stripper 2 and the condenser 3 are interconnected to form a high-pressure synthesis loop. The loop may also comprise a scrubber in some embodiments. The items in the synthesis loop operate at the same or substantially the same pressure, which is preferably in the range 120 to 180 bar.

The FIGURE illustrates a preferred embodiment wherein the high-pressure loop does not include a scrubber. Accordingly the vent gas 16 withdrawn from the reactor 1 goes directly into the condenser 3 after mixing with the portion of stripper vapours 152.

It can also be noted that fresh CO2 enters said loop only via the line 12 connected to the stripper 2. In other words the only input of fresh is the CO2 entering the stripper 2 as stripping medium.

The fresh ammonia enters the loop from line 22 connected to the ejector 6 and possibly from line 17 which mixes with the stream 152 before the condenser 3. In the event that ammonia enters from both locations, it is preferred that the majority of ammonia enters via the ejector, i.e. from line 22.

In a variant the gas vented from the reactor 1 via line 16 may be sent to a high-pressure scrubber and washed with a carbamate solution, e.g. a portion of the solution 18. The liquid effluent from the scrubber may be sent to the tube side of the condenser 3.

What is claimed is:

1. A process for the synthesis of urea from ammonia and carbon dioxide in a stripping process comprising a synthesis section including at least a reactor, a stripper, and a condenser, the process comprising:
   converting ammonia and carbon dioxide into urea in the reactor at a synthesis pressure and forming an aqueous reactor effluent containing urea and unconverted ammonium carbamate;
   stripping the aqueous reactor effluent in the stripper by heating and contacting said aqueous reactor effluent with gaseous carbon dioxide acting as a stripping aid, and forming a urea-containing solution and stripper vapours predominantly composed of ammonia and carbon dioxide;
   sending the urea-containing solution effluent from the stripper to a low-pressure recovery section and further processing the urea-containing solution effluent from the stripper in said low-pressure recovery section;
   wherein the gaseous carbon dioxide fed to the stripper represents the full input of fresh carbon dioxide to the synthesis section;
   splitting the stripper vapours into a first portion which is sent to the reactor and a second portion which is sent to the condenser,
   wherein the condenser is a shell-and-tube kettle condenser with a tube side and a shell side and said second portion of the stripper vapours is sent to the tube side and condensed to form a carbamate-containing condensate stream; and
   withdrawing the carbamate-containing condensate stream from the tube side of the condenser and returning the carbamate-containing condensate stream to the reactor.

2. The process according to claim 1, wherein returning said carbamate-containing condensate stream to the reactor comprises feeding said carbamate-containing condensate stream to a carbamate separator to separate a carbamate-containing liquid from the carbamate-containing condensate stream, and returning said carbamate-containing liquid to the reactor.

3. The process according to claim 2, wherein said carbamate-containing liquid, which is obtained in the carbamate separator, is sent to the reactor via an ejector together with fresh ammonia.

4. The process according to claim 3, wherein the fresh ammonia fed to the ejector represents the majority of fresh ammonia input to the synthesis section.

5. The process according to claim 1, wherein prior to introduction into the tube side of the condenser, the second portion of stripper vapours is mixed with a stream of fresh ammonia and/or with a carbamate-containing recycle solution coming from said low-pressure recovery section.

6. The process according to claim 1, wherein the urea synthesis section does not include a high-pressure scrubber and a stream of inert gas vented from the reactor is mixed with the second portion of stripper vapours prior to introduction of said stripper vapours into the tube side of the condenser.

7. The process according to claim 4, wherein another portion of fresh ammonia input to the synthesis section is mixed with the second portion of stripper vapours before introduction of said stripper vapours into the tube side of the condenser.

8. The process according to claim 1, wherein the shell side of the condenser is traversed by a cooling fluid.

9. The process according to claim 1, wherein the urea is synthesized at a pressure of 120 bar to 180 bar, and the low-pressure recovery is performed at a pressure of 2 to 6 bar.

10. A $CO_2$-stripping urea plant comprising:
a synthesis loop including at least a reactor, a stripper and a condenser;
a line arranged to feed a urea-containing reactor effluent from the reactor to the stripper, and a line arranged to feed fresh $CO_2$ as a stripping medium to said stripper;
a line arranged to send a urea-containing solution effluent from the stripper to a low-pressure recovery section for further processing,
said line arranged to feed fresh $CO_2$ to the stripper being the only $CO_2$ feed of the synthesis loop,
a line arranged to feed a first portion of stripper overhead vapours to the reactor, and a line arranged to feed a second portion of said stripper vapours to the condenser,
the condenser being a shell-and-tube kettle condenser with a tube side and a shell side and said line arranged to feed the second portion of the stripper vapours to the condenser being connected to the tube side of the condenser, so that the second portion of stripper vapours is fed into the tube side of the condenser for condensation,
a line arranged to withdraw a carbamate-containing condensate stream from the tube side of the condenser.

11. The plant according to claim 10, further comprising a carbamate separator arranged to separate the carbamate-containing condensate stream withdrawn from the tube side of the condenser into a carbamate-containing liquid, and a line that recycles the carbamate-containing liquid to the reactor, and a gas phase.

12. The plant according to claim 11, further including an ejector arranged to feed the carbamate containing liquid from the carbamate separator to the urea reactor, and a line arranged to feed fresh ammonia as a motive stream to the ejector.

13. The plant according to claim 10, further including one or more lines arranged to mix the second portion of stripper vapours, prior to its introduction into the tube side of the condenser, with a stream of fresh ammonia and/or with a carbamate-containing recycle solution coming from the recovery section.

14. The plant according to claim 10, wherein the synthesis loop does not include a high-pressure scrubber and a line is arranged to mix a stream of inert gas vented from the reactor with the second portion of stripper vapours prior to introduction of said stripper vapours into the tube side of the condenser.

15. The plant according to claim 10, wherein the urea reactor is a vertical reactor having a height of less than 20 meters.

16. The process according to claim 8, wherein the cooling fluid comprises boiling water.

17. The process according to claim 8, wherein the cooling fluid is at a pressure not greater than 6 bar.

18. The process according to claim 8, wherein the cooling fluid is at a pressure of 2 to 6 bar.

19. The process according to claim 9, wherein the low-pressure recovery is performed at a pressure of 4 bar.

20. The plant according to claim 15, wherein the height of the urea reactor is in the range of 12 to 18 meters.

* * * * *